US010473573B2

(12) United States Patent
Chung et al.

(10) Patent No.: US 10,473,573 B2
(45) Date of Patent: Nov. 12, 2019

(54) PARTICULATE MATTER SENSOR AND EXHAUST GAS PURIFICATION SYSTEM USING THE SAME

(71) Applicant: AMOTECH CO., LTD., Incheon (KR)

(72) Inventors: Yeon-Soo Chung, Incheon (KR); Soo-Min Oh, Seoul (KR); Eun-Ji Kim, Incheon (KR); Sung-Eun Jo, Gunpo-si (KR); Yang-Joo Ko, Seongnam-si (KR); Jung-Taek Kim, Bucheon-si (KR); Heon-Joon Park, Uiwang-si (KR); Tae-Kwan Yi, Anyang-si (KR)

(73) Assignee: AMOTECH CO., LTD., Incheon (KR)

( * ) Notice: Subject to any disclaimer, the term of this patent is extended or adjusted under 35 U.S.C. 154(b) by 39 days.

(21) Appl. No.: 15/140,066

(22) Filed: Apr. 27, 2016

(65) Prior Publication Data
US 2016/0363522 A1 Dec. 15, 2016

(30) Foreign Application Priority Data
Jun. 9, 2015 (KR) .................... 10-2015-0081390

(51) Int. Cl.
*G01N 15/06* (2006.01)
*F02M 26/04* (2016.01)
(Continued)

(52) U.S. Cl.
CPC ......... *G01N 15/0656* (2013.01); *F01N 3/021* (2013.01); *F01N 9/002* (2013.01);
(Continued)

(58) Field of Classification Search
CPC ................................................ G01N 15/0656
(Continued)

(56) References Cited

U.S. PATENT DOCUMENTS 6,634,210 B1 * 10/2003 Bosch ............... G01N 15/0656
                                                        204/426
8,225,640 B2 * 7/2012 Nelson ............. G01N 15/0656
                                                        73/28.01
(Continued)

FOREIGN PATENT DOCUMENTS

DE     10 2006 055 520 A1    5/2008
JP        2009-085959 A      4/2009
(Continued)

*Primary Examiner* — John Fitzgerald
*Assistant Examiner* — Rodney T Frank
(74) *Attorney, Agent, or Firm* — Seed Intellectual Property Law Group LLP

(57) ABSTRACT

A particulate matter sensor and an exhaust gas purification system using the same are provided. A particular matter sensor according to some embodiments of the present invention includes a first insulation layer including a first electrode unit exposed on a first side thereof, which includes a plurality of first electrodes not electrically connected to each other, a second insulation layer arranged in parallel to the first insulation layer with a space therebetween, including a second electrode unit on a first side thereof, which includes a plurality of second electrodes electrically connected to each other, a temperature sensing unit formed on a first side of a third insulation layer located on a second side of the second insulation layer, and a heater unit formed on a first side of a fourth insulation layer located on a second side of the third insulation layer, the heater unit configured to heat the first and second electrode units. One of the first electrodes is configured to be electrically connected to a first electrical contact terminal. The second electrodes are electrically connected to a second electrical contact terminal. The first electrodes and the second electrodes are arranged respectively corresponding to each other. The first electrodes are configured to be electrically connected to each other by particulates deposited therebetween to allow capacitance (Continued)

between the first electrode and the second electrode to be changed.

7 Claims, 5 Drawing Sheets

(51) Int. Cl.
<br>*F01N 3/021* (2006.01)
<br>*F01N 11/00* (2006.01)
<br>*F01N 13/10* (2010.01)
<br>*G01M 15/10* (2006.01)
<br>*F01N 9/00* (2006.01)
<br>*G01N 15/00* (2006.01)
<br>*F01N 3/10* (2006.01)

(52) U.S. Cl.
<br>CPC ............ *F01N 11/002* (2013.01); *F01N 13/10* (2013.01); *F02M 26/04* (2016.02); *G01M 15/102* (2013.01); *G01N 15/0606* (2013.01); *F01N 3/103* (2013.01); *F01N 2560/05* (2013.01); *F01N 2560/08* (2013.01); *F01N 2560/20* (2013.01); *G01N 2015/0046* (2013.01); *Y02T 10/20* (2013.01); *Y02T 10/47* (2013.01)

(58) Field of Classification Search
<br>USPC ........................................................ 73/23.33
<br>See application file for complete search history.

(56) References Cited

U.S. PATENT DOCUMENTS

2007/0119233 A1* 5/2007 Schnell ............. G01N 15/0656
<br>73/28.01
2009/0090622 A1* 4/2009 Ripley ............... G01N 15/0656
<br>204/401

FOREIGN PATENT DOCUMENTS

| JP | 2010-190615 A | 9/2010 |
| JP | 2011-247650 A | 12/2011 |
| JP | 2012-127907 A | 7/2012 |
| JP | 2013-117381 A | 6/2013 |

* cited by examiner

PARTICULATE MATTER SENSOR AND EXHAUST GAS PURIFICATION SYSTEM USING THE SAME

TECHNICAL FIELD

The present disclosure relates to a particulate matter sensor and an exhaust gas purification system using the same.

BACKGROUND

In general, with tightening of emission control, an aftertreatment apparatus for purifying an exhaust gas takes a growing interest. In particular, the emission control is being more tightened on particulate matter (PM) from a diesel car.

Specifically, the emission control on exhaust pollutant included in the exhaust gas is increasingly tightened due to a demand on a healthy environment and an environmental regulation of each country against air pollutant, and as a countermeasure for this situation, various exhaust gas purification methods are being studied.

To this end, an aftertreatment technology for treating the exhaust gas has been proposed, which includes exhaust gas reduction apparatuses employing oxidation catalyst, nitrogen oxide catalyst, and diesel particulate filter.

Among the above-mentioned exhaust gas reduction apparatuses employing the oxidation catalyst, the nitrogen oxide catalyst, and the diesel particulate filter, the most efficient and commercially-available technology is the exhaust gas reduction apparatus employing the diesel particulate filter.

In order to diagnose malfunctioning of the exhaust gas reduction apparatus, a resistor-type particulate matter sensor (PM sensor) is installed at a post-stage of the DPF filter. That is, the particulate matter (PM) is deposited between electrodes on a surface of the sensor, due to which a current is generated between the electrodes and electrical conductivity of the sensor is changed.

However, such a resistor-type particulate matter sensor has a very slow response speed at the initial stage until the current is generated, and when a particulate matter having the electrical conductivity, such as a metal, is deposited on the surface, generates a distortion of a signal regardless of the amount of the particulate matter, which causes malfunctioning of the sensor.

Patent Document 1: Japanese Patent Application Laid-Open No. 2009-85959 (Publication Date: Apr. 23, 2009)

DISCLOSURE

Technical Problem

It is an object of the present invention to provide a particulate matter sensor that is capable of preventing damage of the sensor even when an electrically-conductive foreign matter is deposited on the sensor and an exhaust gas purification system using the particulate matter sensor.

SUMMARY

In order to solve the above-mentioned problem, a particulate matter sensor according to some embodiments of the present invention includes a first insulation layer including a first electrode unit exposed on a first side thereof, which includes a plurality of first electrodes not electrically connected to each other, a second insulation layer arranged in parallel to the first insulation layer with a space therebetween, including a second electrode unit on a first side thereof, which includes a plurality of second electrodes electrically connected to each other, a temperature sensing unit formed on a first side of a third insulation layer located on a second side of the second insulation layer, and a heater unit formed on a first side of a fourth insulation layer located on a second side of the third insulation layer, the heater unit configured to heat the first and second electrode units. One of the first electrodes is configured to be electrically connected to a first electrical contact terminal. The second electrodes are electrically connected to a second electrical contact terminal. The first electrodes and the second electrodes are arranged respectively corresponding to each other. The first electrodes are configured to be electrically connected to each other by particulates deposited therebetween to allow capacitance between the first electrodes and the second electrodes to be changed.

In some embodiments, the first electrodes and the second electrodes are arranged in parallel the first and second insulation layers in the longitudinal direction, respectively, and the first electrodes and the second electrodes are arranged respectively corresponding to each other in the lateral direction of the first and second insulation layers.

In some embodiments, upon the particulate matter being deposited gradually between the first electrodes, the first electrodes are configured to be electrically connected to each other, increasing an area of the first electrode, to allow the capacitance between the first electrode and the second electrode to be increased.

In some embodiments, the particulate matter sensor further includes a dielectric layer between the first insulation layer and the second insulation layer.

In some embodiments, the first insulation layer and the dielectric layer include a first via hole for electrically connecting the second electrodes to the second electrical contact terminal.

In some embodiments, the fourth insulation layer includes a third electrical contact terminal and a fourth electrical contact terminal configured to be electrically connected to the heater unit and a fifth electrical contact terminal not electrically connected to the third and fourth electrical contact terminals, and the third insulation layer includes second via holes for electrically connecting the temperature sensing unit to the third electrical contact terminal and the fifth electrical contact terminal on the fourth insulation layer, respectively.

In some embodiments, an area of the temperature sensing unit is set within an area of the heater unit.

An exhaust gas purification system according to some embodiments of the present invention includes an exhaust manifold, an exhaust gas particle filter configured to remove particles included in an exhaust gas from the exhaust manifold, and a particulate matter sensor arranged on an exhaust pipe connected to the exhaust gas particle filter and configured to sense particulate matter flowing to a downstream side through the exhaust gas particle filter. The particulate matter sensor includes a first insulation layer including a first electrode unit exposed on a first side thereof, which includes a plurality of first electrodes not electrically connected to each other, a second insulation layer arranged in parallel to the first insulation layer with a space therebetween, including a second electrode unit on a first side thereof, which includes a plurality of second electrodes electrically connected to each other, a temperature sensing unit formed on a first side of a third insulation layer located on a second side of the second insulation layer, and a heater unit formed on a first side of a fourth insulation layer located on a second side of the third insulation layer, the heater unit configured to heat the first and second electrode units. One of the first electrodes is configured to be electrically connected to a first electrical contact terminal. The second electrodes are electrically connected to a second electrical contact terminal. The first electrodes and the second electrodes are arranged respectively corresponding to each other. The first electrodes are configured to be electrically connected to each other by particulates deposited therebetween to allow capacitance between the first electrode and the second electrode to be changed.

Advantageous Effects

The particulate matter sensor used in the exhaust gas purification system according to some embodiments of the present invention is capable of preventing the particulate matter sensor from being damaged due to a distortion of a signal of the sensor by providing a plurality of first electrodes and allowing particulate matter including the electrically-conductive foreign matter to be deposited in a part of spaces formed between the first electrodes and measuring a capacitance between the first electrode unit and the second electrode unit.

DETAILED DESCRIPTION

Figure 1:
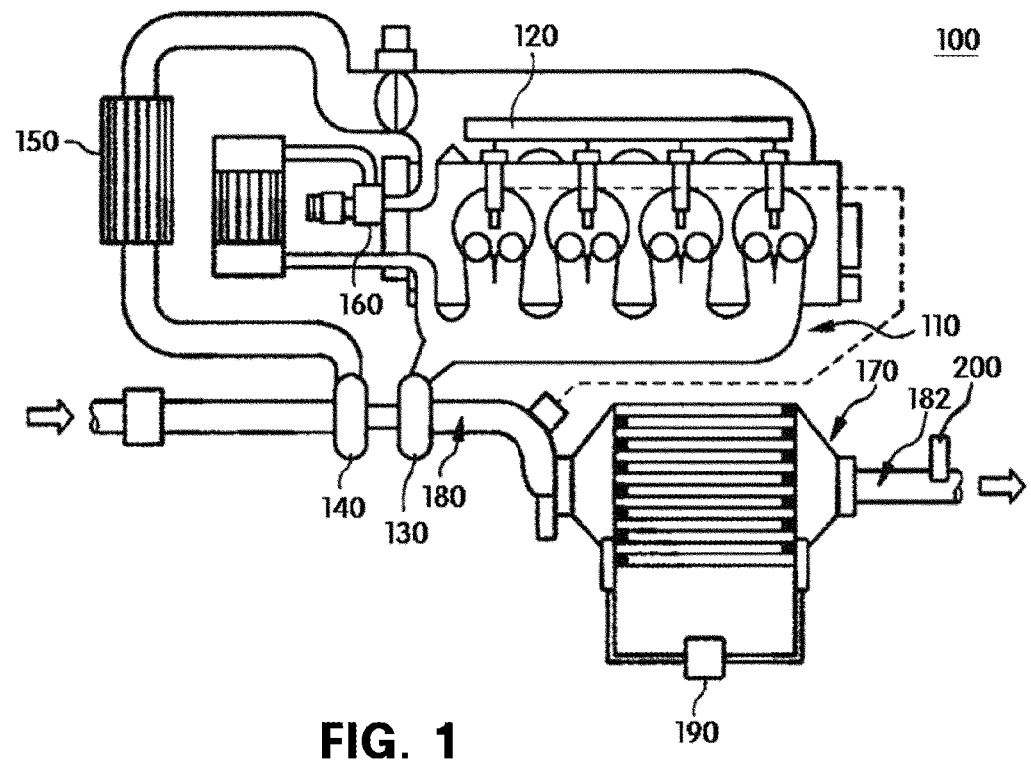
FIG. 1 is a schematic diagram of an exhaust gas purification system for vehicle diesel engine.

Exemplary embodiments of the present invention are described in detail below with reference to the accompanying drawings. The present invention can be applied with various modifications and have various modes, and hence specific embodiments are instantiated on the drawings and described in detail in the specification. However, this does not intend to limit the present invention to specific embodiments, by should be understood to include all modifications, equivalents, and substitutes within the gist or idea of the disclosure and the technical range of the disclosure. In the drawings, parts not relevant to the detailed description of the present invention are omitted. In the following descriptions of the drawings, like reference numerals are assigned to like constituent elements.

Employing an exhaust gas purification system 100 according to the present invention shown in FIG. 1, a turbine 130 is coupled to an exhaust manifold 120 of an engine 110, and when a turbocharger 140 interlocked with the turbine 130 rotates, compressed air is supplied to an intake manifold (not shown) through a cooler 150. A part of combustion air exhaust from the exhaust manifold 120 can be backflown to the intake manifold (now shown) through a valve 160.

A diesel oxidation catalyst (not shown) and an exhaust gas particle filter 170 is coupled to an exhaust pipe 180 that is coupled to the exhaust manifold 120, to treat combustion exhaust gas. That is, in the combustion exhaust gas discharged to the exhaust pipe 180, uncombusted hydrocarbon (HC), carbon monoxide (CO), and nitrogen monoxide (NO) can be oxidized while passing through diesel oxidation catalyst (not shown) on the upstream side, and soot, soluble organic fraction (SOF), and particulate matter including inorganic component can be collected while passing through the exhaust gas particle filter 170 on the downstream side.

The diesel oxidation catalyst (not shown) can increase exhaust temperature by oxidation combustion of supplied fuel and remove SOF components in the particulate matter by oxidation when forcibly regenerating the exhaust gas particle filter 170. Further, $NO_2$ generated by oxidation of NO is used as an oxidizing agent for the particulate matter deposited on the exhaust gas particle filter 170 at the later stage, enabling a continuous oxidation.

The exhaust gas particle filter 170 includes a plurality of holes formed penetrating through a cell wall that partitions gas flow paths, and captures particulate matter in the exhaust gas flown into the exhaust gas particle filter 170. The exhaust gas particle filter 170 can be alternatively configured as a continuous regeneration type diesel particulate filter including diesel oxidation catalyst integrated with the exhaust gas particle filter 170.

A differential pressure sensor 190 can be coupled to the exhaust pipe 180 in order to monitor the amount of the particulate matter deposited on the exhaust gas particle filter 170. The differential pressure sensor 190 is connected to the upstream side and the downstream side of the exhaust gas particle filter 170, and can output a signal depending on a pressure difference therebetween.

Further, temperature sensors (not shown) are provided on the upstream side of the diesel oxidation catalyst and the downstream and the downstream sides of the exhaust gas particle filter 170 in order to monitor the exhaust temperatures at the respective places.

A control circuit (now shown) monitors catalyst activation state of the diesel oxidation catalyst and collecting state of the particulate matter in the exhaust gas particle filter 170 based on outputs of the above-mentioned devices, and when the collecting amount of the particulate matter exceeds a predetermined tolerance, executes a forced regeneration to perform a regeneration control for removing the particulate matter by combustion.

A particulate matter sensor 200 is installed on an output-side exhaust pipe 182 connected to the other side of the exhaust gas particle filter 170, and senses the particulate matter flowing to the downstream side by penetrating through the exhaust gas particle filter 170.

Figure 2:
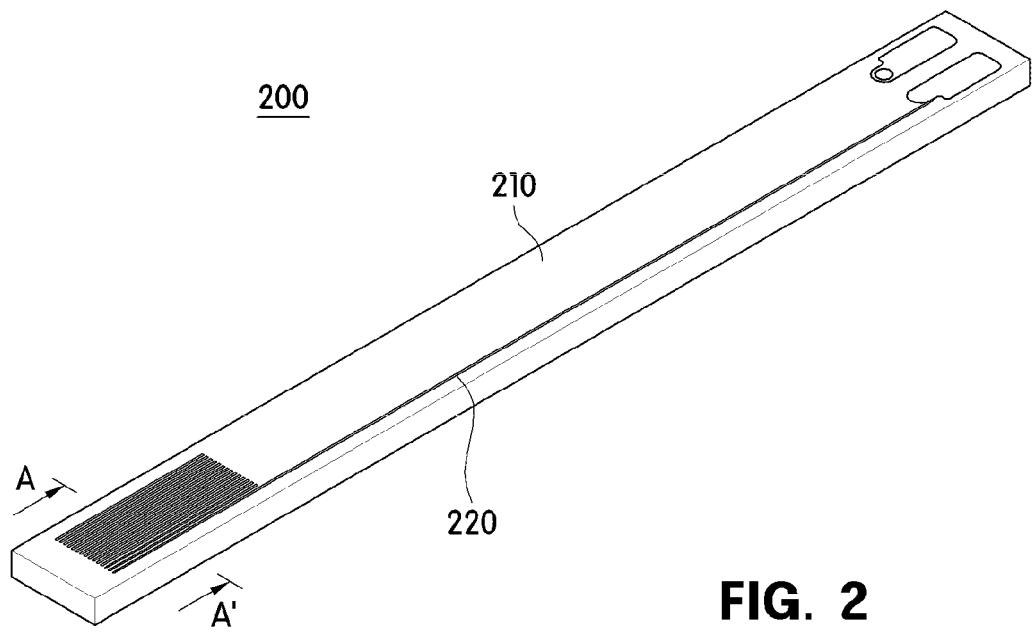
FIG. 2 is a perspective view of a particulate matter sensor according to some embodiments of the present invention.
Figure 3:
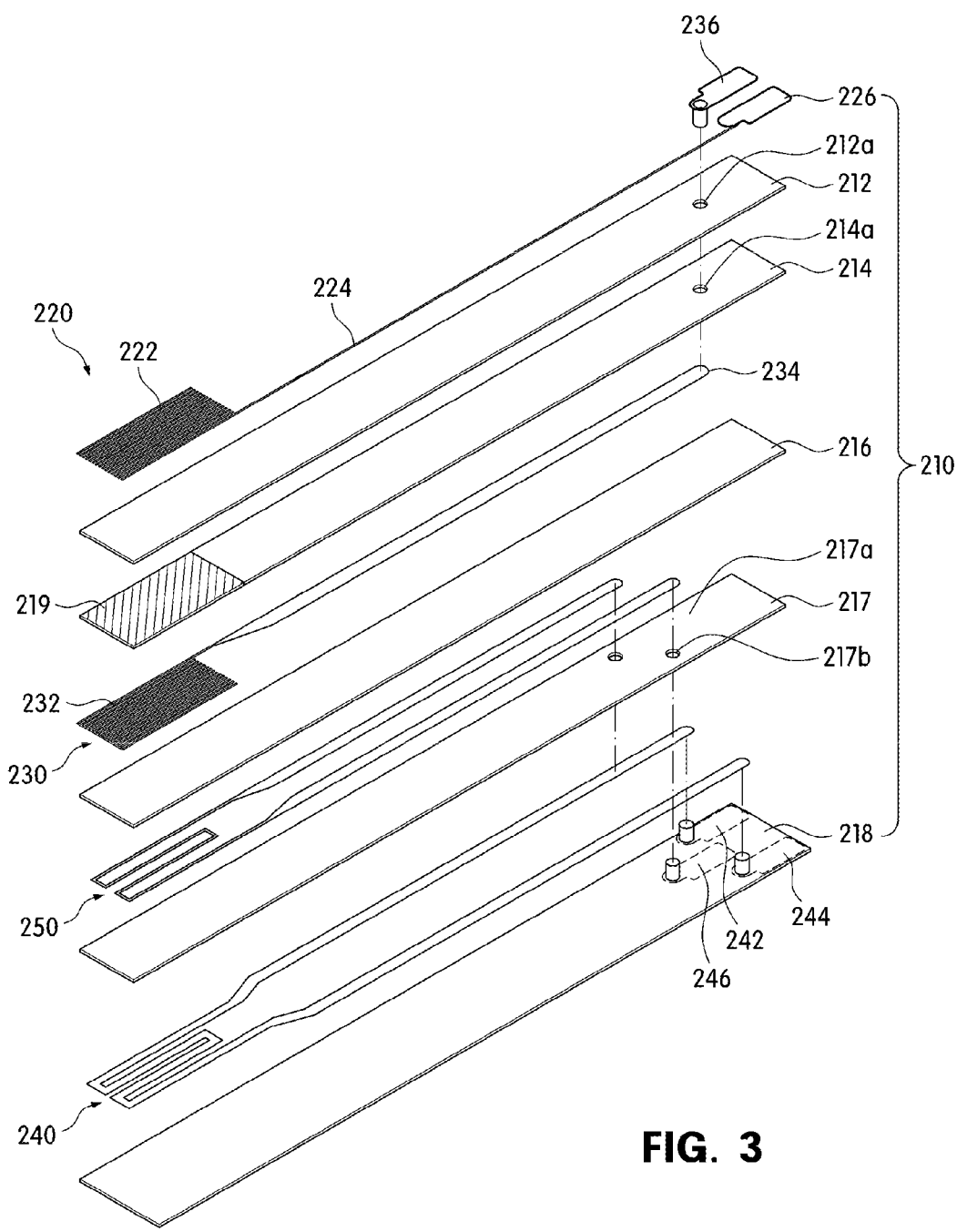
FIG. 3 is an exploded perspective view of the particulate matter sensor shown in FIG. 2.

The particulate matter sensor 200 according to the present invention shown in FIGS. 2 and 3 includes an insulated board 210, a first electrode unit 220, a second electrode unit 230, a heater unit 240, and a temperature sensing unit 250.

The insulated board 210 includes a plurality of insulation layers 212, 214, 216, 217, and 218 laminated in parallel, which is formed of heat-resistant insulation member such as glass material, ceramic material, aluminum, spinel, or titanium dioxide.

Specifically, the fifth insulation layer 214 between the first and second insulation layers 212 and 216 among the insulation layers 212, 214, 216, 217, and 218 constituting the insulated board 210 may include a dielectric layer 219 having dielectric permittivity.

The dielectric layer 219 may be arranged between a first electrode 222 and a second electrode 232.

Specifically, the dielectric layer 219 may be arranged between the first electrode 222 and the second electrode 232 in order to achieve good capacitive property, and be formed of ceramic material.

As shown in FIGS. 2 and 3, the first electrode unit 220 may be formed being exposed on a surface of the insulated board 210. Specifically, the first electrode unit 220 may be formed on the first insulation layer 212 that is the top layer among the insulation layers 212, 214, 216, 217, and 218.

The first electrode unit 220 may include a plurality of first electrodes 222, a first electrode lead 224, and a first electrical contact terminal 226, and the first electrodes 222 may be formed in linear shape in parallel to each other at regular intervals on the surface of the first insulation layer 212 on one side.

Figure 4A:
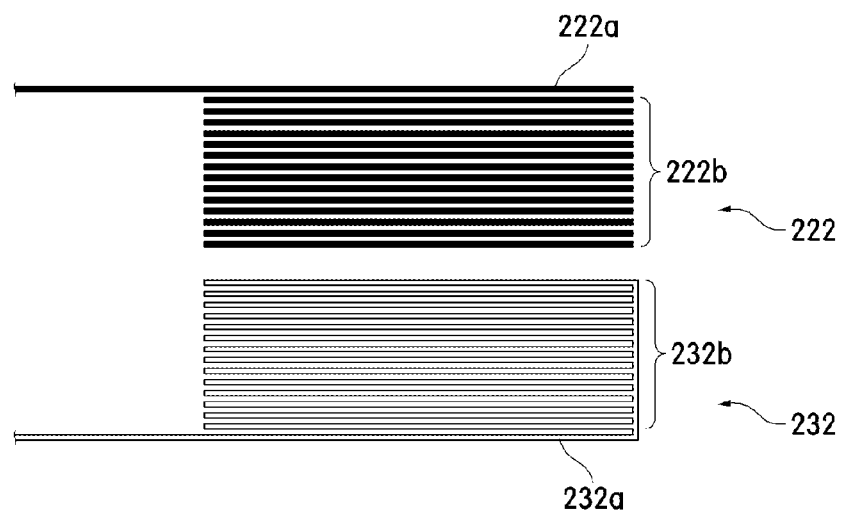
FIGS. 4A and 4B are plan views of first and second electrode units shown in FIGS. 2 and 3.

As shown in FIG. 4A, a first electrode 222a formed on the outer side among the first electrodes 222 may be electrically connected to the first electrical contact terminal 226 via the first electrode lead 224, and the rest of the first electrodes 222b are not electrically connected to each other.

The second electrode unit 230 may be formed on a surface of the second insulation layer 216 on one side, which is arranged in parallel to the first insulation layer 212.

The second electrode unit 230 may include a plurality of second electrodes 232, a second electrode lead 234, and a second electrical contact terminal 236, and the second electrodes 232 may be formed in linear shape in parallel to each other at regular intervals on the surface of the second insulation layer 216 on one side.

In this case, the second electrodes 232 may be electrically connected to each other, and a second electrode 232a among the second electrodes 232 may be electrically connected to the second electrical contact terminal 236 via the second electrode lead 234.

In particular, the first insulation layer 212 includes a first via hole 212a and the fifth insulation layer 214 includes a via hole 214a for electrically connecting the second electrodes 232 to the second electrical contact terminal 236.

As shown in FIG. 4A, the first electrodes 222 included in the first electrode unit 220 and the second electrodes 232 included in the second electrode unit 230 are formed corresponding to each other respectively on the first and second insulation layers 212 and 216, in an overlapped manner in parallel to each other.

Figure 4B:
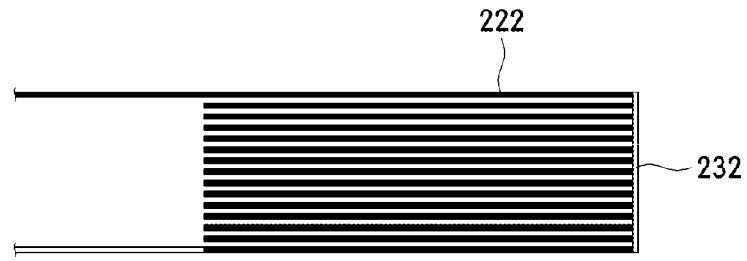
Figure 6:
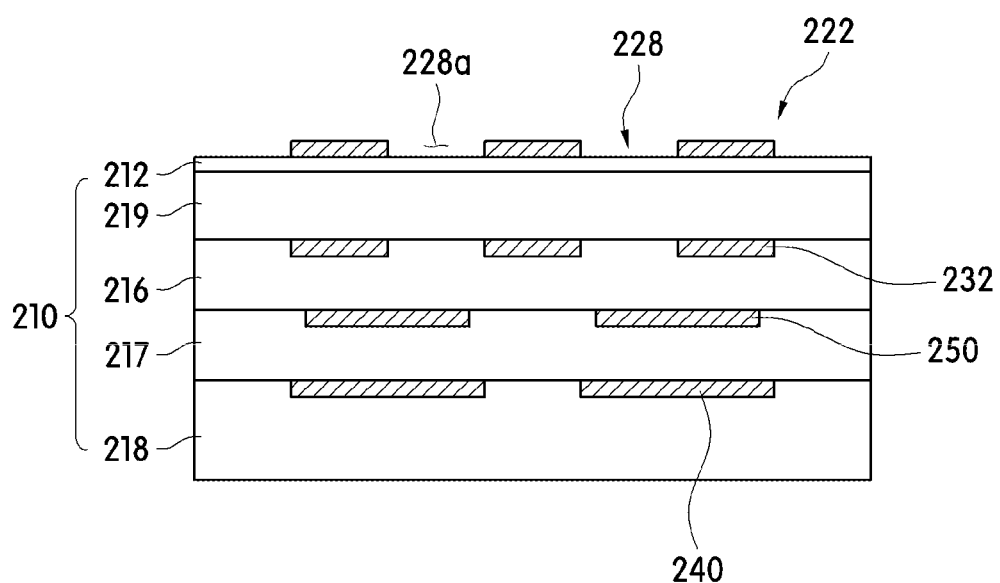
FIG. 6 is an enlarged cross-sectional view of the particulate matter sensor cut along a line A-A' shown in FIG. 2.

Specifically, as shown in FIGS. 4B and 6, the first electrodes 222 and the second electrodes 232 are arranged in parallel to the first and second insulation layers 212 and 216 in the longitudinal direction, and the first electrodes 222 and the second electrodes 232 are arranged respectively corresponding to each other in the lateral direction of the first and second insulation layers 212 and 216.

Further, spaces are formed between the first electrodes 222, and particulate matter can be deposited in the spaces 228 formed between the first electrodes 222.

Specifically, the particulate matter is gradually deposited from a first space 228a among the space 228 included in the first electrode unit 220, and eventually, deposited in the entire space 228.

The first electrodes 222 are then electrically connected by the deposited particulate matter, and hence the conductive area of the first electrode 222 is gradually increased, which allows the change of the capacitance between the first electrode unit 220 and the second electrode unit 230 to be measured.

Details on the method of measuring the capacitance is described later with reference to FIG. 7.

The fourth insulation layer 218 may include the heater unit 240 for heating the first and second insulation layers 212 and 216 and the dielectric layer 219.

Both terminals of the heater unit 240 may be electrically connected to a third electrical contact terminal 244 and a fourth electrical contact terminal 242 formed on the fourth insulation layer 218.

The heater unit 240 may be installed to remove the particulate matter deposited on the first electrode unit 220, and specifically, when the heater unit 240 heats the first electrode unit 220 for a predetermined time at a predetermined temperature, the particulate matter deposited on the first electrode unit 220 can be removed.

As temperature of the exhaust environment after the exhaust gas particle sensor (170 in FIG. 1) is as high as about 300° C. or more and becomes 650° C. or more when the heater is turned on, a normal metal has a high probability of being oxidized when being used as a material for the heater unit, and hence a material that is hard to be oxidized at a high temperature is used as the material for the heater unit 240.

The temperature sensing unit 250 is provided to measure temperatures of the first and second insulation layers 212 and 216 and the dielectric layer 219, which may be formed on the third insulation layer 217, and more specifically, arranged between the second electrode unit 230 and the heater unit 240.

Both ends of the temperature sensing unit 250 may be electrically connected to the fourth electrical contact terminal 242 and a fifth electrical contact terminal 246 via second via holes 217a and 217b, respectively.

Specifically, a first end of the temperature sensing unit 250 may be electrically connected to the fourth electrical contact terminal 242 to which a first end of the heater unit 240 is connected, and a second end of the temperature sensing unit 250 may be electrically connected to the fifth electrical contact terminal 246 formed on the fourth insulation layer 218.

In this case, the fifth electrical contact terminal 246 formed on the fourth insulation layer 218 is not electrically connected to the third electrical contact terminal 244 and the fourth electrical contact terminal 242.

The heater unit 240 for heating the first and second insulation layers 212 and 216 can be controlled by comparing the temperature measured by the temperature sensing unit 250 with a temperature measured by a temperature sensor (not shown) installed in a vehicle.

Figure 5:
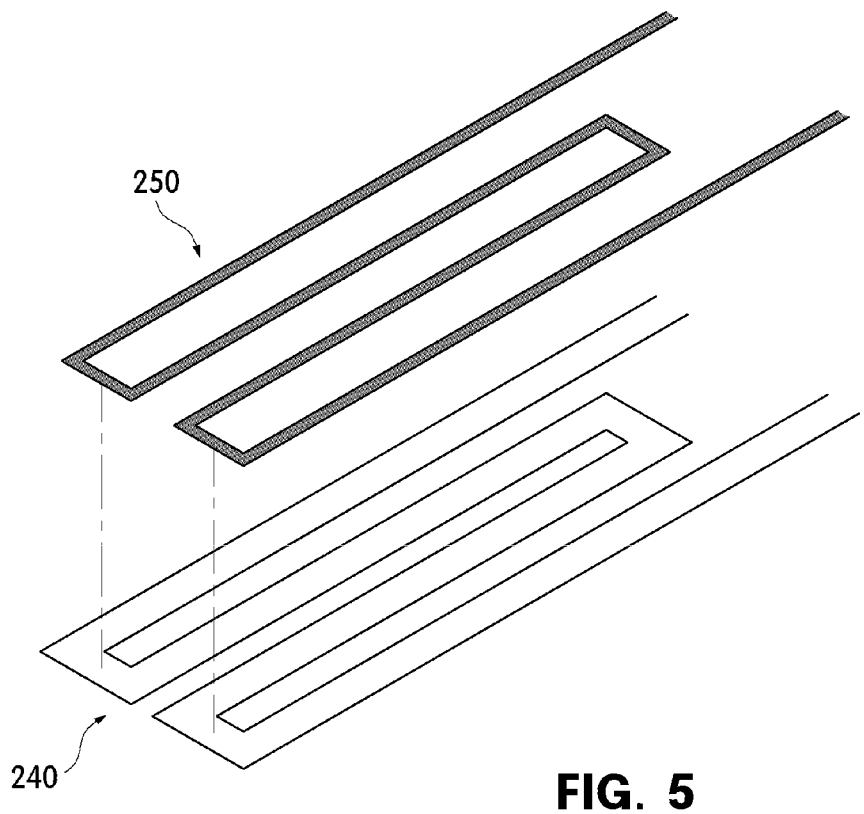
FIG. 5 is a plan view of a heater unit and a temperature sensing unit shown in FIGS. 2 and 3.

An installation area of the temperature sensing unit 250 may be set to locate within an installation area of the heater unit 240. For example, as shown in FIG. 5, the area of the temperature sensing unit may be formed equal to or smaller than the area of the heater unit 240.

Figure 7:
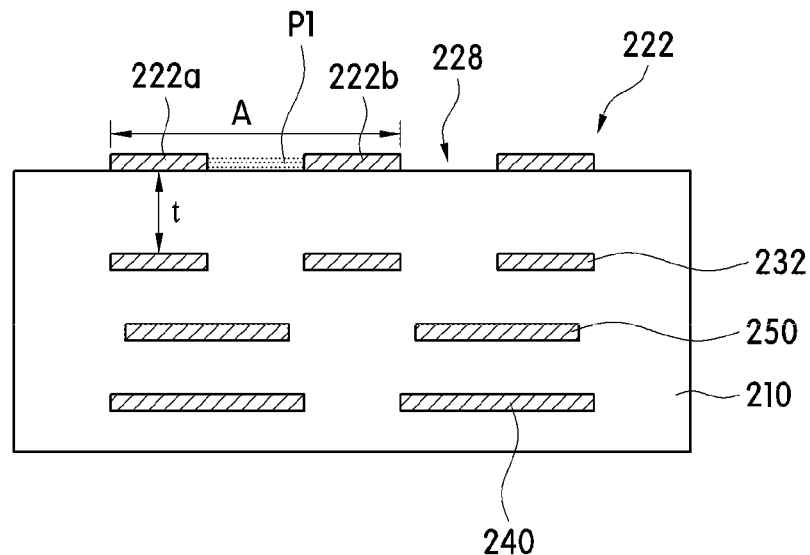
FIG. 7 is a cross-sectional view of the particulate matter sensor according to some embodiments of the present invention for illustrating an operation state thereof.
Figure 8:
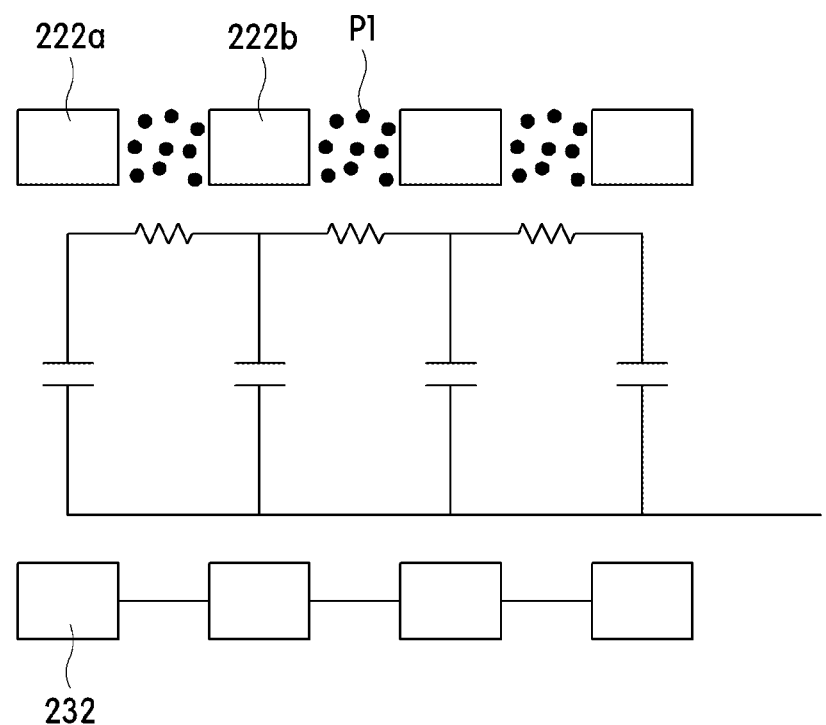
FIG. 8 is a schematic diagram of the first electrode unit and the second electrode unit of the particulate matter sensor according to some embodiments of the present invention.

As shown in FIGS. 7 and 8, particulate matter P1 flown to the output-side exhaust pipe 182 via the exhaust gas particle filter (170 in FIG. 1) passes near the particulate matter sensor 200 installed on one side of the output-side exhaust pipe 182, and at this time, the particulate matter P1 may be deposited in the spaces 228 formed between the first electrodes 222.

Specifically, the first electrode 222a and the first electrode 222b neighboring the first electrode 222a among the first electrodes 222 are electrically connected to each other by the particulate matter deposited between the first electrode 222a and the first electrode 222b so that the area of the first electrode 222 through which the current flows is increased, and then the capacitance between the first electrode 222 and the second electrode 232 is changed.

The capacitance between the first electrode 222 and the second electrode 232 can be measured by $C=\varepsilon A/t$, where A is area of the first electrodes 222a and 222b located on both sides of the space 228 in which the particulate matter P1 is deposited, t is distance between the first electrodes 222 in which the particulate matter P1 is deposited and the second electrodes 232, and hence the capacitance between the first electrode unit 220 and the second electrode unit 230 can be measured.

Whenever the particulate matter P1 is deposited gradually from the first space among the spaces 228 formed in the first electrode unit 220, the first electrodes 222 become electrically connected to each other, and hence the area of the first electrodes 222 is gradually increased.

With the increase of the area of the first electrodes 222, the first electrodes 222 are electrically connected to each other, and then the capacitance between the first electrode unit 220 and the second electrode unit 230 may be increased accordingly.

For example, when three first electrodes 222 are formed on the insulated board 210, the area of each of the first electrodes 222 is 1, and the area of the space 228 is 1, an area A of the capacitance can take the minimum of 1 to the maximum of 5, and the magnitude of the capacitance may be increased from the minimum of 1 to the maximum of 5 accordingly.

That is, with the assumption that the area of an arbitrary first electrode 222a is constant, the capacitance can be increased in proportion to the ear of the spaces 228, and by controlling the area of the first electrodes 222 and the area of the deposited particulate matter by a user, the magnitude of the capacitance can be adjusted to a value desired by the user.

Therefore, the particulate matter sensor that is employed in the exhaust gas purification system can be prevented from being damaged due to distortion of a signal of the sensor by measuring the capacitance between the first electrode unit and the second electrode unit, which is changed by particulate matter including electrically conductive foreign matter and deposited in a part of space formed between the first electrodes.

Although exemplary embodiments of the present disclosure have been described for illustrative purposes, those skilled in the art will appreciate that various modifications, additions and substitutions are possible, without departing from the idea and scope of the claimed disclosure. Accordingly, one of ordinary skill would understand the scope of the claimed disclosure is not to be limited by the explicitly described above embodiments but by the claims and equivalents thereof.

[PARTS]

| | |
|---|---|
| 100: Exhaust gas purification system | |
| 110: Engine | 120: Exhaust manifold |
| 130: Turbine | 140: Turbocharger |
| 150: Cooler | 160: Valve |
| 170: Exhaust gas particle filter | |
| 180: Exhaust pipe | 182: Outlet-side Exhaust pipe |
| 190: Differential pressure sensor | |
| 200: Particulate matter sensor | |
| 210: Insulated board | 220: First electrode unit |
| 222: First Electrode | 224: First electrode lead |
| 226: First electrical contact terminal | |
| 230: Second electrode unit | |
| 232: Second electrode | 234: Second electrode lead |
| 236: Second electrical contact terminal | |
| 240: Heater unit | 250: Temperature sensing unit |

The invention claimed is:

1. A particulate matter sensor, comprising:
first, second, third, and fourth insulation layers laminated together,
the first insulation layer including a first electrode unit on a first side thereof, the first electrode unit exposed to particulate matter during operation of the particulate matter sensor, and the first electrode unit including a plurality of first electrodes not electrically connected to each other;
the second insulation layer arranged in parallel to the first insulation layer with a space therebetween, the second insulation layer including a second electrode unit on a first side thereof that faces a second side of the first insulation layer opposite the first side of the first insulation layer such that the second electrode unit is not exposed to particulate matter during operation of the particulate matter sensor, the second electrode unit including a plurality of second electrodes electrically connected to each other;
a temperature sensing unit formed on a first side of the third insulation layer located on a second side of the second insulation layer; and
a heater unit formed on a first side of the fourth insulation layer located on a second side of the third insulation layer, the heater unit configured to heat the first and second electrode units, wherein
each of the plurality of second electrodes is spaced apart from a lower portion of the plurality of the first electrodes so as to overlap and correspond to each other with each of the plurality of first electrodes,
the plurality of first electrodes are electrically connected to each other by the particulate matter deposited in a space formed between two neighboring first electrodes, and
a capacitance between the first electrodes and the second electrodes is increased by enlarging an area of the first electrodes electrically connected to each other when the particulate matter is deposited between the first electrodes.

2. The particulate matter sensor according to claim 1, wherein
the first electrodes and the second electrodes are arranged in parallel to the first and second insulation layers in a longitudinal direction, respectively, and
the first electrodes and the second electrodes are arranged respectively corresponding to each other in a lateral direction of the first and second insulation layers.

3. The particulate matter sensor according to claim 1, further comprising a dielectric layer between the first insulation layer and the second insulation layer.

4. The particulate matter sensor according to claim 3, wherein the first insulation layer and the dielectric layer include a first via hole for electrically connecting the second electrodes to a second electrical contact terminal.

5. The particulate matter sensor according to claim 4, wherein
the fourth insulation layer includes
a third electrical contact terminal and a fourth electrical contact terminal configured to be electrically connected to the heater unit, and
a fifth electrical contact terminal not electrically connected to the third and fourth electrical contact terminals, and
the third insulation layer includes second via holes for electrically connecting the temperature sensing unit to the third electrical contact terminal and the fifth electrical contact terminal on the fourth insulation layer, respectively.

6. The particulate matter sensor according to claim 1, wherein an area of the temperature sensing unit is set within an area of the heater unit.

7. An exhaust gas purification system, comprising:
an exhaust manifold;
an exhaust gas particle filter configured to remove particles included in an exhaust gas from the exhaust manifold; and
a particulate matter sensor arranged on an exhaust pipe connected to the exhaust gas particle filter and configured to sense particulate matter flowing to a downstream side through the exhaust gas particle filter, wherein
the particulate matter sensor includes first, second, third, and fourth insulation layers laminated together,
the first insulation layer including a first electrode unit on a first side thereof, the first electrode unit exposed to particulate matter during operation of the particulate matter sensor, and the first electrode unit including a plurality of first electrodes not electrically connected to each other,
the second insulation layer arrange in parallel to the first insulation layer with a space therebetween, the second insulation layer including a second electrode unit on a first side thereof that faces a second side of the first insulation layer opposite the first side of the first insulation layer such that the second electrode unit is not exposed to particulate matter during operation of the particulate matter sensor, the second electrode unit including a plurality of second electrodes electrically connected to each other,
a temperature sensing unit formed on a first side of the third insulation layer located on a second side of the second insulation layer, and
a heater unit formed on a first side of the fourth insulation layer located on a second side of the third insulation layer, the heater unit configured to heat the first and second electrode units, wherein
each of the plurality of second electrodes is spaced apart from a lower portion of the plurality of the first electrodes so as to overlap and correspond to each other with each of the plurality of the first electrodes,
the plurality of first electrodes are electrically connected to each other by the particulate matter deposited in a space formed between two neighboring first electrodes, and
a capacitance between the first electrodes and the second electrodes is increased by enlarging an area of the first electrodes electrically connected to each other when the particulate matter is deposited between the first electrodes.

* * * * *